United States Patent [19]

Pellico

[11] Patent Number: 4,781,923

[45] Date of Patent: Nov. 1, 1988

[54] ANTISEPTIC GELS

[76] Inventor: Michael A. Pellico, 3024 Military Ave., Los Angeles, Calif. 90272

[21] Appl. No.: 75,440

[22] Filed: Jul. 20, 1987

[51] Int. Cl.$^4$ .............................................. A61K 33/40
[52] U.S. Cl. ..................................................... 424/130
[58] Field of Search ......................................... 424/130

[56] References Cited

U.S. PATENT DOCUMENTS

| | | | |
|---|---|---|---|
| 3,639,574 | 1/1972 | Schmoeka | 424/130 X |
| 3,954,974 | 5/1976 | Heryog et al. | 424/130 |
| 4,071,508 | 1/1978 | Steckler | 526/262 X |
| 4,428,933 | 1/1984 | King | 424/130 X |
| 4,431,631 | 2/1984 | Clipper et al. | 424/130 X |
| 4,438,102 | 3/1984 | Ganci | 424/130 |
| 4,518,585 | 5/1985 | Greene et al. | 424/130 |
| 4,557,935 | 12/1985 | Af Ekenstam et al. | 424/130 |

FOREIGN PATENT DOCUMENTS

| | | | |
|---|---|---|---|
| 0146807 | 8/1985 | Japan | 424/130 |
| 1158907 | 7/1986 | Japan | 424/130 |
| 0647145 | 1/1985 | Switzerland | 424/130 |
| 2068225 | 8/1981 | United Kingdom | 424/130 |
| 2076285 | 12/1981 | United Kingdom | 424/130 |
| 2076286 | 12/1981 | United Kingdom | 424/130 |

*Primary Examiner*—Nancy A. B. Swisher
*Attorney, Agent, or Firm*—Donald Diamond

[57] ABSTRACT

An antiseptic gel composition comprising polyglycerylmethacrylate hydrate gel and hydrogen peroxide is prepared by admixing an aqueous solution of hydrogen peroxide with polyglycerylmethacrylate hydrate gel so as to provide a gel composition containing from about 0.5 to about 15 wt. % hydrogen peroxide. The composition is stable and, at a suitable hydrogen peroxide concentration, is adapted for adherent application to infectious dermal sites.

20 Claims, No Drawings

ANTISEPTIC GELS

BACKGROUND OF THE INVENTION

1. Field of the Invention

This invention relates to antiseptic compositions and, more particularly, to antiseptic gels incorporating hydrogen peroxide as an antiseptic agent.

2. Prior Art

Aqueous solutions containing hydrogen peroxide at a concentration level from about 1 to about 10% have long been known for their antiseptic properties. While it is reported in the literature that the antiseptic characteristics of hydrogen peroxide arise by virtue of the oxidizing properties of this composition, it has also been suggested that the mode of action of hydrogen peroxide is through the production of a strong oxidant, namely, the hydroxyl free radical. However, the early use of low concentration, hydrogen peroxide solutions as antiseptic compositions led to unfavorable results because the solutions tended to be unstable and the application of such solutions to tissue containing significant levels of catalase resulted in rapid deactivation of the hydrogen peroxide.

More recently, there has been an upsurge of interest in the utilization of hydrogen peroxide solutions as antiseptic compositions. These solutions are generally available as aqueous compositions containing 3.0 wt. % hydrogen peroxide. However, these aqueous compositions have certain disadvantages. One notable disadvantage is in the application of the liquid composition to skin cuts or abrasions where the amount utilized compared to the amount poured is minimal since most of the liquid immediately flows away from the application site. Another problem encountered with the liquid is that it is difficult to apply to certain areas of the body and must be cautiously applied to other areas of the body as, for example, in the vicinity of the eyes. Also, since hydrogen peroxide solutions may degrade faster when agitated, there utilization as carry-on antiseptic compositions in camping, hiking, and like activities is limited.

Accordingly, it would be advantageous to provide a stable and adherent hydrogen peroxide composition which overcomes the disadvantages that are present in the aqueous hydrogen peroxide solutions.

SUMMARY OF THE INVENTION

In accordance with one aspect of this invention, there is provided an antiseptic gel composition comprising polyglycerylmethacrylate hydrate gel and hydrogen peroxide.

In accordance with a second aspect of this invention, there is provided a method for preparing an antiseptic gel composition which comprises admixing an aqueous solution of hydrogen peroxide with polyglycerylmethacrylate hydrate gel.

In accordance with a third aspect of this invention, there is provided a method for treating an infectious site which comprises applying to the infectious site an antiseptic gel composition comprising polyglycerylmethacrylate hydrate gel and hydrogen peroxide.

DETAILED DESCRIPTION

The antiseptic gel compositions of this invention comprise polyglycerylmethacrylate hydrate gel and hydrogen peroxide. The polyglycerylmethacrylate hydrate gel which can be utilized in this invention is available under the trademark Lubrajel from Guardian Chemical Corporation, 230 Marcus Blvd., Hauppauge, Long Island, N.Y. 11787. The gel is characterized as a clathrate formed by the reaction of sodium glycerate with an acrylic acid polymer, stablized with a small amount of propylene glycol, followed by controlled hydration of the resulting product.

The product specification for LUBRAJEL, which has the CTFA Name, "Polyglycerylmethacrylate and propylene glycol," is as follows:

| SPECIFICATION | CHARACTERISTIC |
| --- | --- |
| Form | Viscous gel |
| pH (as is) | 5.0–6.0 |
| Viscosity, in cps at 20° C. (Brookfield RTV) | 300,000–400,000 |
| Color | colorless |
| Clarity | clear |
| Specific gravity | 1.3 g./ml. |
| Water solubility | complete |
| Conductivity, expressed as resistance to current flow in micromho/cm | 80–90 |
| Loss of weight, %, on exposure to air in glass beakers at 20° C., 18 months, 70% R.H. | 16–18 |
| Decomposition at 250° F./1 hr. | practically none |
| Color change when exposed to 250° F. for 1 hour | colorless to straw |
| Shelf stability (sealed), on storage for 3 years at 20° C., % undecomposed | 100% |

Hydrogen peroxide is advantageously incorporated into the hydrated polymeric gel complex as a constituent of an aqueous solution of hydrogen peroxide as, for example, an aqueous solution containing about 35 wt. % hydrogen peroxide.

The antiseptic gel can be further formulated with optional, special purpose additives such as humectants, emollients, local anesthetics, nonionic surfactants, buffers, and the like, as well as enzymatic inhibitors specific to enzymes which effect rapid degradation of hydrogen peroxide. Illustrative humectants include glycerol, sorbitol and hydrated starch solutions; an illustrative emollient is wintergreen oil; an illustrative local anesthetic is benzocaine.

Hydrogen peroxide is generally present in the antiseptic gel in an amount from about 0.5 to about 15 wt. % and, preferably, in an amount from about 1 to about 11 wt. %. The concentration of polygylcerylmethacrylate hydrate is so selected as to provide the antiseptic gel composition with a desired consistency. In general, polygylcerylmethacrylate hydrate is present in the antiseptic gel in an amount from about 45 to about 96 wt. %. Water and any optional additives make up the balance of the composition to 100 wt. %.

The antiseptic gel compositions can be prepared by admixing an aqueous solution of hydrogen peroxide and any optional additives with polygylcerylmethacrylate hydrate wherein the amount of hydrogen peroxide solution is so selected as to provide the antiseptic gel with a hydrogen peroxide concentration from about 0.5 to about 15 wt. % and, preferably with a hydrogen peroxide concentration from about 1 to about 11 wt. %. The admixing step is advantageously carried out in plastic, stainless steel or glass lined vessels with a mixer suitable for use with compositions having a gel consistency. The polygylcerylmethacrylate hydrate is generally present in the admixing step in an amount from about 45 to about 96 wt % with water and any optional additives comprising the balance of the ingredients to 100 wt. %.

The antiseptic gel composition comprising polygylcerylmethacrylate hydrate and hydrogen peroxide is used by applying it to an infectious site where, in contrast to aqueous hydrogen peroxide solutions, it does not flow away or run off from the area of application. Accordingly, its gel characteristics are such that it is safer to use if the area of application is near the eyes or any other body area which should not be in contact with hydrogen peroxide. Also, the hydrogen peroxide gel can be more effective than hydrogen peroxide solutions because the gel can remain in contact with the area of application longer than the liquid. A further advantage of the antiseptic gel over the hydrogen peroxide solution is that the gel forms a protective-type coating over the affected area.

EXAMPLES

The following examples further illustrate the invention. As used in the examples, "Lubrajel" is the trademark for polyglycerylmethacrylate hydrate gel stablized with a small amount of propylene glycol and the expression "Hydrogen peroxide (35%)" designates an aqueous solution containing 35 wt. % hydrogen peroxide.

EXAMPLE 1

This example illustrates an antiseptic gel containing 3.0 wt. % hydrogen peroxide.

| COMPOSITION | PARTS BY WEIGHT |
|---|---|
| Lubrajel | 10.6 |
| Hydrogen Peroxide (35%) | 1.0 |

EXAMPLE 2

This example illustrates an antiseptic gel containing 1.5 wt. % hydrogen peroxide.

| COMPOSITION | PARTS BY WEIGHT |
|---|---|
| Lubrajel | 11.1 |
| Hydrogen Peroxide (35%) | 0.5 |

EXAMPLE 3

This example illustrates a low viscosity antiseptic gel containing 3.0 wt. % hydrogen peroxide.

| COMPOSITION | PARTS BY WEIGHT |
|---|---|
| Lubrajel | 5.6 |
| Water (deionized) | 5.0 |
| Hydrogen Peroxide (35%) | 1.0 |

EXAMPLE 4

This example illustrates an antiseptic gel that incorporates a humectant to provide the gel with enhanced moisturizing properties.

| COMPOSITION | PARTS BY WEIGHT |
|---|---|
| Lubrajel | 5.6 |
| Glycerol (U.S.P.) | 5.6 |
| Hydrogen Peroxide (35%) | 1.0 |

EXAMPLE 5

This example illustrates an antiseptic gel containing 10.5 wt. % hydrogen peroxide and which is useful for bleaching hair or disinfecting.

| COMPOSITION | PARTS BY WEIGHT |
|---|---|
| Lubrajel | 8.1 |
| Hydrogen Peroxide (35%) | 3.5 |

EXAMPLE 6

This example illustrates an antiseptic gel containing 3.0 wt. % hydrogen peroxide, a humectant and a local anesthetic.

| COMPOSITION | PARTS BY WEIGHT |
|---|---|
| Lubrajel | 6.0 |
| Hydrogen Peroxide (35%) | 1.0 |
| Water (Deionized) | 1.5 |
| Oleic acid decyl ester | 1.5 |
| FD&C Color Red #40 | 0.003 |
| Benzocaine | 0.5 |

EXAMPLE 7

This example illustrates an antiseptic gel containing 3.0 wt. % hydrogen peroxide and an emollient to provide a soothing effect.

| COMPOSITION | PARTS BY WEIGHT |
|---|---|
| Lubrajel | 10.0 |
| Hydrogen Peroxide (35%) | 1.0 |
| Wintergreen | 0.6 |

As to the compositions of this invention, it is important to note that hydrogen peroxide is an oxidizing agent and Lubrajel is moderately acidic and, accordingly, it is important to take these characteristics into consideration in the selection of optional additives for incorporation into the antiseptic gels. Also, it is important to select optional additives that do not have a significant adverse effect on either hydrogen peroxide or Lubrajel. In this connection, the use of salt in the formulation should be limited in order to avoid degradation of Lubrajel.

In view of the foregoing description and examples, it will become apparent to those of ordinary skill in the art that equivalent modifications thereof may be made without departing from the spirit and scope of this invention That which is claimed is:

1. An antiseptic gel composition comprising polyglycerylmethacrylate hydrate gel and hydrogen peroxide.

2. The composition of claim 1 wherein the concentration of hydrogen peroxide is from about 0.5 to about 15 wt. %.

3. The composition of claim 1 wherein the concentration of hydrogen peroxide is from about 1 to about 11 wt. %.

4. The composition of claim 1 which further includes a humectant.

5. The composition of claim 1 which further includes an emollient.

6. The composition of claim 1 which further includes a local anesthetic.

7. A method for preparing an antiseptic gel composition which comprises admixing an aqueous solution of hydrogen peroxide with polyglycerylmethacrylate hydrate gel.

8. The method of claim 7 wherein the amount of hydrogen peroxide solution is so selected as to provide the antiseptic gel with a hydrogen peroxide concentration from about 0.5 to about 15 wt. %.

9. The method of claim 7 wherein the amount of hydrogen peroxide solution is so selected as to provide the antiseptic gel with a hydrogen peroxide concentration from about 1 to about 11 wt. %.

10. The method of claim 7 wherein the polyglycerylmethacrylate hydrate gel has a viscosity from about 300,000 to about 400,000 centipoises at 20° C.

11. The method of claim 7 wherein the polyglycerylmethacrylate hydrate gel has a specific gravity of about 1.3 grams per milliliter.

12. The method of claim 7 which further includes admixing a humectant with said gel.

13. The method of claim 7 which further includes admixing an emollient with said gel.

14. The method of claim 7 which further includes admixing a local anesthetic with said gel.

15. A method for treating an infectious site which comprises applying to said site an antiseptic gel composition containing polyglycerylmethacrylate hydrate gel and hydrogen peroxide.

16. The method of claim 15 wherein the concentration of hydrogen peroxide in the antiseptic gel is from about 0.5 to about 15 wt. %.

17. The method of claim 15 wherein the concentration of hydrogen peroxide in the antiseptic gel is from about 1 to about 11 wt. %.

18. The method of claim 15 wherein the antiseptic gel further includes a humectant.

19. The method of claim 15 wherein the antiseptic gel further includes an emollient.

20. The method of claim 15 wherein the antiseptic gel further includes a local anesthetic.

* * * * *